(12) United States Patent
Nguyen

(10) Patent No.: US 6,713,644 B1
(45) Date of Patent: Mar. 30, 2004

(54) HYDROSILATION WITH PLATINUM FREE NEAT COPPER CONTAINING CATALYST

(75) Inventor: Binh Thanh Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 9 days.

(21) Appl. No.: 10/264,881

(22) Filed: Oct. 3, 2002

(51) Int. Cl.$^7$ .............................. C07F 7/08; C07F 7/12; C07F 7/14; C07F 7/16
(52) U.S. Cl. ........................ 556/479; 556/481
(58) Field of Search ................... 556/481, 479

(56) References Cited

U.S. PATENT DOCUMENTS

| | | | |
|---|---|---|---|
| 5,103,033 A | * | 4/1992 | Bank ........................ 556/415 |
| 6,177,585 B1 | | 1/2001 | Chen et al. ................ 556/479 |
| 6,500,977 B1 | * | 12/2002 | Dinh et al. ................ 556/479 |

FOREIGN PATENT DOCUMENTS

JP    J50069022    6/1975

OTHER PUBLICATIONS

"The Condensation Reaction of Trichlorosilane with Allylic Chlorides Catalyzed by Copper Salts in the Presence of a Teritary Amine", Journal of OrganoMet. Chem, 1975, by Furuya, N.; Sukawa, T.; Abstract.

* cited by examiner

Primary Examiner—Peter O'Sullivan
(74) Attorney, Agent, or Firm—Jim L. DeCesare

(57) ABSTRACT

Chloropropylsilanes are prepared via hydrosilation of olefinic halides with organosilicon hydrides, in the presence of neat platinum free copper containing catalysts. Organosilicon hydrides such as triethylsilane, olefinic halides such as allyl chloride, and catalysts such as copper acetate, copper chloride, copper sulphate, copper hydroxide, copper nitrate, and copper cyanide, can be used in the process.

6 Claims, No Drawings

HYDROSILATION WITH PLATINUM FREE NEAT COPPER CONTAINING CATALYST

FIELD OF THE INVENTION

This invention is related to hydrosilation processes in which organosilicon hydrides are caused to react with olefinic halides using certain inorganic catalysts.

BACKGROUND OF THE INVENTION

It is known to react certain silicon hydrides with olefinic halides using catalysts containing copper to prepare organosilanes, i.e., T. Sukawa and N. Furuya, *Journal of Organometallic Chemistry*, (1975) Volume 96 (1). Thus, according to Sukawa, such a reaction proceeds as follows: $Cl_3SiH+H_2C=CHCH_2Cl+(C_2H_5)_3N+CuCl \rightarrow Cl_3SiCH_2C(CH_3)=CH_2+Cl_3SiCH_2CH=CHCH_3+(C_2H_5)_3N \cdot HCl$.

However, Sukawa fails to disclose using organosilicon hydrides such as trialkylsilanes $R_3SiH$, or alkoxyalkylsilanes such as $R_2(RO)SiH$ and $R(RO)_2SiH$, where R is an alkyl group having 1–20 carbon atoms, in place of the trichlorosilane. Thus, in the present invention, organosilicon hydrides such as triethylsilane are reacted with olefinic halides such as allyl chloride, using neat copper containing catalysts, to prepare organosilicon compounds such as 3-chloropropyltriethylsilane. The reaction proceeds generally according to the equation: $(C_2H_5)_3SiH + H_2C=CHCH_2Cl+CuCl$ (neat) $\rightarrow (C_2H_5)_3SiCH_2CH_2CH_2Cl$. Neat catalysts are required because of the tendency of tertiary amines to be reactive with certain silanes.

While U.S. Pat. No. 6,177,585 (Jan. 23, 2001) shows hydrosilation reactions for preparing organosilicon compounds using (i) triethylsilane as the silicon hydride, (ii) allyl chloride as the unsaturated reactant, i.e., the olefinic halide, and (iii) catalysts containing copper as surface segregating metal components of the catalysts, the catalyst in the '585 patent contains platinum as the actual active hydrosilating metal.

In contrast to the '585 patent, however, according to the present invention (i) triethylsilane is reacted with (ii) allyl chloride using (iii) neat copper containing catalysts that are free of platinum for the preparation of organosilicon compounds such as 3-chloropropyltriethylsilane. The particular type of catalyst (iii) that is used in this invention is required because of the discovery that the hydrosilation of olefinic halides such as allyl chloride with $\equiv$SiH compounds using platinum containing catalysts can result in forming undesired by-products such as n-propylsilane, rather than desired products such as chloropropylsilane.

The reason this occurs is believed to be that allyl chloride decomposes in the presence of platinum metal to form propylene, which then undergoes hydrosilation to the undesired by-products including n-propylsilanes. Thus, platinum catalysts are capable of causing isomerization of terminal C=C bonds in olefinic halides to internal C=C bonds, e.g., hexadiene, allyl chloride, and 1,3-butadiene, and result in the formation of undesired by-products.

The advantage of using a platinum free copper containing catalysts is that undesired by-products are eliminated. In particular, therefore, the prior art fails to disclose using neat platinum free copper containing catalysts as the active hydrosilating metal in the hydrosilation process.

SUMMARY OF THE INVENTION

This invention is directed to a hydrosilation process in which an organosilicon hydride is reacted with an olefinic halide in the presence of a catalyst. The improvement consists of using a neat platinum free copper containing catalyst.

Organosilicon hydrides such as triethylsilane, olefinic halides such as allyl chloride, and catalysts such as copper acetate, copper chloride, copper sulphate, copper hydroxide, copper nitrate, and copper cyanide, can be used in the process.

These and other features of the invention will become apparent from a consideration of the detailed description.

DETAILED DESCRIPTION OF THE INVENTION

Hydrosilation is a reaction involving the addition of a silicon hydride to unsaturated hydrocarbons to form silicon-carbon bonds. It is a process used to commercially prepare various organofunctional silicon monomers, to crosslink silicone polymers, and to connect various silicon containing structural units to organic polymer blocks for forming copolymers. One simplified example is hydrosilation of α-olefins with silicon hydrides according to the reaction: $\equiv SiH+CH_2=CH-R \rightarrow \equiv SiCH_2CH_2-R$.

Organosilicon hydrides suitable for use according to the present invention are compounds generally corresponding to the formula $R_3SiH$ wherein R is an alkyl group containing 1–20 carbon atoms such as methyl, ethyl, isopropyl, t-butyl, octyl, decyl, and n-octadecyl. R can also represent alkoxy groups or alkoxyalkyl groups such as methoxy, ethoxy, butoxy, methoxymethyl, ethoxymethyl, methoxyethyl, ethoxyethyl, and ethoxypropyl; or R can be a cycoalkyl group such as dicyclopentylmethyl, cyclopentyldimethyl, dicyclohexylmethyl, or cyclohexyldimethyl.

Some representative examples of organosilicon hydrides are t-butyldimethylsilane, dicyclopentylmethylsilane, dicyclohexylmethylsilane, dicyclobutylethylsilane, diethylmethylsilane, ethyldimethylsilane, n-octadecyldimethylsilane, tri-t-butylsilane, triethoxysilane, triethylsilane, triisopropylsilane, trimethoxysilane, trimethylsilane, trioctylsilane, and tri-n-propylsilane.

Olefinic halides suitable for use herein are exemplified by compounds such as allyl chloride, 3-chloro-1-butene, 1-chloro-3-methyl-2-butene, 3-chloro-2-methylpropene, and vinyl chloride.

The preferred catalyst according to this invention is a neat platinum free copper containing catalyst which can be exemplified by compounds such as copper acetate, copper chloride, copper sulphate, copper hydroxide, copper nitrate, and copper cyanide. The term neat, for purposes of this invention, is intended to mean that the copper containing catalyst is used in its undiluted form. Thus, the copper containing catalyst is not dissolved, dispersed, combined with, or mixed with another substance or ingredient including (i) nonpolar hydrocarbon solvents such as benzene, toluene, and xylene; (ii) polar solvents such as water, glycols, and esters; (iii) tertiary amines; or (iv) carriers. Thus, the copper containing catalyst should be used in its substantially pure form.

The relative amount of organosilicon hydride and olefinic halide used according to the invention can be varied. While one unsaturated carbon-carbon linkage per silicon bonded hydrogen atom is stoichiometric, there is no requirement that the reaction be carried out under stoichiometric conditions. It is preferred that the reaction be conducted using a stoichiometric excess of the organosilicon hydride. Most preferred, therefore, is to carry out the reaction using about a 0.1–10 percent stoichiometric excess of the organosilicon hydride.

Contact between the organosilicon hydride, the olefinic halide, and the neat platinum free copper containing catalyst, can occur at a temperature between 0–350° C., preferably between 60–250° C., and most preferably at a temperature of about 200° C.

The optimum reaction time is variable depending upon the reactants, the reaction temperature, and the concentration of the catalyst. Ordinarily, there is no benefit in extending the contact time of the reactants beyond about 48 hours, but likewise there is usually no harm, unless extremely elevated temperatures are employed. With most of the particular reactants used herein, practical quantitative yields can be obtained about 45 hours.

The reaction can be carried out at atmospheric, sub-atmospheric, or super-atmospheric pressure. Here again, the choice of conditions is largely a matter of logic, based upon the nature of the reactants, and the equipment available. Non-volatile reactants are especially adaptable to being heated at atmospheric pressure with or without a reflux arrangement. Reactants which are gaseous at ordinary temperatures are preferably reacted at substantially constant volume under autogenous or induced pressure. The best results are obtained by maintaining all reactants in the liquid phase.

The following example is set forth in order to illustrate the invention in more detail. In particular, it was found that at 200° C. and in about 45 hours, triethylsilane reacted with allyl chloride, in the presence of a neat platinum free copper containing catalyst, to yield quantitatively, the compound 3-chloropropyltriethylsilane.

The results and the data determined under these reaction conditions are shown in Table 1. In Table 1, $Et_3SiH$ represents triethylsilane, $ClPrSiEt_3$ represents the desired end product 3-chloropropyltriethylsilane, and GC represents Gas Chromatography, the analytical method used for making these determinations.

EXAMPLE 1

A master solution was prepared containing 4 gram/0.034 mole of triethylsilane and 3.12 gram/0.04 mole of allyl chloride. Each reaction was carried out using 0.6 gram of the master solution. The reaction with each of the copper catalyst was conducted in a ten inch PYREX® glass tube with an outside diameter of 12 millimeter. The copper catalyst was added to the glass tube. A pipette was used to add the master solution necessary to establish the mole ratio of copper catalyst/triethylsilane as shown in Table 1. The glass tube was cooled in an ice bath containing dry ice and isopropyl alcohol. The glass tube was sealed and heated to about 200° C. for about 45 hours. Heating was discontinued, the glass tube was cooled in the ice bath, and opened. The reaction mixture present in the glass tube was analyzed by Gas Chromatography (GC), and the GC results were reported as GC area percent.

TABLE 1

| Copper Catalyst | Mole Ratio of Copper Catalyst to $Et_3SiH$ | GC Area Percent of $ClPrSiEt_3$ | GC Area Percent of Unreacted $Et_3SiH$ |
| --- | --- | --- | --- |
| Copper Chloride | $2.6 \times 10^{-2}$ | 77.8 | 0 |
| Copper Acetate | $2.6 \times 10^{-2}$ | 82.6 | 0 |
| Copper Sulphate | $2.6 \times 10^{-2}$ | 26.0 | 40.9 |
| No Catalyst | N/A | 20.0 | 48 |

Table 1 shows that copper catalysts, especially copper chloride and copper acetate, and copper sulphate, are effective in catalyzing the hydrosilation of allyl chloride with triethylsilane, at 200° C. for 45 hours, yielding quantitatively 3-chloropropyltriethylsilane.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. In a hydrosilation process in which an organosilicon hydride is reacted with an olefinic halide in the presence of a catalyst, the improvement which comprises the catalyst being a neat platinum free copper containing catalyst.

2. The process according to claim 1 in which the organosilicon hydride is a compound having the formula $R_3SiH$ in which R is an alkyl group containing 1–20 carbon atoms, an alkoxy group, an alkoxyalkyl group, or a cycloalkyl group.

3. The process according to claim 2 in which the organosilicon hydride is a compound selected from the group consisting of t-butyldimethylsilane, dicyclopentylmethylsilane, dicyclohexylmethylsilane, dicyclobutylethylsilane, diethylmethylsilane, ethyldimethylsilane, n-octadecyldimethylsilane, tri-t-butylsilane, triethoxysilane, triethylsilane, triisopropylsilane, trimethoxysilane, trimethylsilane, trioctylsilane, and tri-n-propylsilane.

4. The process according to claim 1 in which the olefinic halide is a compound selected from the group consisting of allyl chloride, 3-chloro-1-butene, 1-chloro-3-methyl-2-butene, 3-chloro-2-methylpropene, and vinyl chloride.

5. The process according to claim 1 in which the neat platinum free copper containing catalyst is a compound selected from the group consisting of copper acetate, copper chloride, copper sulphate, copper hydroxide, copper nitrate, and copper cyanide.

6. The process according to claim 1 in which the organosilicon hydride is triethylsilane, the olefinic halide is allyl chloride, and the catalyst is copper acetate or copper chloride.

\* \* \* \* \*